(12) United States Patent
Kojima

(10) Patent No.: US 6,852,495 B2
(45) Date of Patent: Feb. 8, 2005

(54) PROCESS OF EXTRACTING NUCLEIC ACID AND PROCESS OF SIMULTANEOUSLY CARRYING OUT EXTRACTION AND PURIFICATION OF NUCLEIC ACID

(75) Inventor: Kouichi Kojima, Tokyo (JP)

(73) Assignees: Shimadzu Corporation, Kyoto (JP); Agriculture Forestry and Fisheries Technical Information, Tokyo (JP)

( * ) Notice: Subject to any disclaimer, the term of this patent is extended or adjusted under 35 U.S.C. 154(b) by 2 days.

(21) Appl. No.: 10/448,394

(22) Filed: May 30, 2003

(65) Prior Publication Data

US 2003/0229222 A1 Dec. 11, 2003

(30) Foreign Application Priority Data

Jun. 6, 2002 (JP) .......................................... 2002-166291
Jun. 7, 2002 (JP) .......................................... 2002-166784

(51) Int. Cl.[7] .......................... C12Q 1/68; B01D 11/00; B01F 1/00
(52) U.S. Cl. .......................... 435/6; 210/634; 423/658.5
(58) Field of Search .............................. 435/6; 210/634; 423/658.5

(56) References Cited

U.S. PATENT DOCUMENTS 4,918,178 A   4/1990   Hurley et al.
2002/0068292 A1   6/2002   Kojima

FOREIGN PATENT DOCUMENTS

EP   0338591 A2 *  10/1989
JP   2002-037798 A1   2/2002

OTHER PUBLICATIONS

Vary et al, "Use of Highly Specific DNA Probes and the Polymerase Chain Reaction to Detect *Mycobacterium paratuberculosis* in Johne's Disease" Journal of Clinical Microbiology, May 1990, p. 933–937 vol. 28, No. 5 American Society for Microbiology.

J.W.B. Van Der Giessen et al "Amplification of 16S rRNA sequences to detect *Mycobacterium paratuberculosis*" J. Med. Microbiology, vol. 36 (1992) pp. 255–263 The Pathological Society of Great Britain and Ireland.

* cited by examiner

Primary Examiner—Jezia Riley
(74) Attorney, Agent, or Firm—Rader, Fishman & Grauer PLLC

(57) ABSTRACT

The present invention provides a process of extracting nucleic acid in a simple manner at a high efficiency with no use of any hazardous reagent from biological materials having required specific procedure for nucleic acid extraction, particularly from biological materials such as bacteria of the genus *Mycobacterium;* and a process of simultaneously carrying out the extraction and purification of nucleic acid in a simple manner from such biological materials existing in a biological sample such as feces having involved much difficulty in the purification of the nucleic acid. In the present invention, vigorous agitation of biological materials with fine particles in solutions containing chelating reagents or agitation of biological materials with aqueous solutions containing chelating reagents and quaternary ammonium salts, together with organic solvents and fine particles is performed.

31 Claims, 6 Drawing Sheets

SEQUENCE LISTING

```
<160> NUMBER OF SEQ ID NOS: 2
<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 1
gatcggaacg tcggctggtc agg                                            23

<210> SEQ ID NO 2
<211> LENGTH: 24
```

```
<212> TYPE: DNA
<213> ORGANISM: Artificial Sequence
<220> FEATURE:
<223> OTHER INFORMATION: Description of Artificial Sequence: primer

<400> SEQUENCE: 2
acgacgacgc gcagcgattg ctct                                              24
```

PROCESS OF EXTRACTING NUCLEIC ACID AND PROCESS OF SIMULTANEOUSLY CARRYING OUT EXTRACTION AND PURIFICATION OF NUCLEIC ACID

BACKGROUND OF THE INVENTION

1. Field of the Invention

The present invention relates to a process of preparing nucleic acid so as to recover nucleic acid as a sample for various procedures using nucleic acid, more-specifically to a process of preparing nucleic acid so as to recover the nucleic acids of bacteria and the like such as those of the genus Mycobacterium having been said to involve much difficulty in the extraction from biological samples such as feces having been said to involve much difficulty in the purification.

2. Description of the Related Art
(Extraction Process)

General processes of extracting nucleic acid from biological materials such as viruses, bacteria, fungi, protozoa, plants and animals have been used, such as a process of decomposing cell wall with enzymes such as lysozyme and extracting nucleic acid in solution and a process of decomposing protein with enzymes such as proteinase to destruct cell and then extracting nucleic acid in solution.

However, these extraction processes with enzyme treatment require full skills and times, so these processes are at poor treatment efficiencies, disadvantageously. When these extraction processes are applied to biological materials with hard cell wall, such as bacteria of the genus *Mycobacterium* and fungal spores, the cells cannot be decomposed. Therefore, the nucleic acid extraction efficiency of these processes is extremely low. So as to extract nucleic acid from bacteria of the genus *Mycobacterium*, which involve much difficulty in the destruction of the bacterial cells, the method described in the report of Vary, et al. (J. Clin. Microbiol., 28(5), 933–937, (1990)) requires treating the bacteria with enzymes of three species over 48 hours in total.

So as to overcome the problem that such bacterial cells have such hard cell walls that the bacterial cells involve difficulty in the destruction thereof, accordingly, a process has been known, which includes vigorous agitation of bacterial cells, using phenol and fine particles. For example, the report of Giessen, et al. (J. Med. Microbiol., 36(1992), 255–263) describes a modified approach including a step of destructing the bacterial cells through vigorous agitation together with fine particles of zirconium oxide in TE buffer (10 mM Tris-HCl, 1 mM EDTA) and phenol. Additionally, U.S. Pat. No. 4,918,178 includes a similar description.

However, the extraction process has an advantage of higher extraction efficiency as well as disadvantages of the use of a very hazardous reagent phenol and the pollution of laboratory environment with phenol during the agitation procedure. Therefore, the extraction process is poor in terms of practical applicability.
(Purification Process)

So as to purify nucleic acid from an extract solution of nucleic acid, proteins and lipophilic contaminants in the extract solution of nucleic acid should be removed from the extract solution. Generally, a process has been known, which includes the denaturation and removal of such protein and lipophilic contaminants using phenol/chloroform and the concentration and purification of the resulting nucleic acid fraction via ethanol precipitation and the like. Further, a process of adsorbing nucleic acid on glass beads and the like to remove ingredients except for nucleic acid and a process of filtering off contaminants using filter and the like have been known.

However, especially when a biological sample is feces and the like, the aforementioned purification process occurs problems as follows. For example, by the process of using phenol and chloroform, contaminants other than the lipophilic contaminants cannot be removed; by the process of using glass beads, contaminants in the feces inhibit the adsorption of the nucleic acid on the glass beads; and by the process of using filter, filtration cannot be accomplished due to clogging of the filter with contaminants in the feces. Therefore, nucleic acids with high purity cannot be obtained from feces by these methods.

Indeed, after a process for purifying nucleic acids was performed by treating feces as a sample with enzymes using proteinases followed by conducting the phenol-chloroform extraction, precipitates of the nucleic acids were obtained by an ethanol precipitation method. As a result, the precipitates were yellowish or brownish. This result indicates that contaminants in the feces are not removed and purification of the nucleic acids is not accomplished in high purity.

So as to recover highly pure nucleic acid from feces involving much difficulty in the purification of the nucleic acid therein, the inventors developed a process of purifying nucleic acid using quaternary ammonium salt (JP-A-2002-37798A). According to the process, contaminants derived from feces excluding nucleic acid can be removed at high efficiency.

So as to prepare nucleic acid from an intended sample, a process and a purification process appropriate for the properties of the sample are selected from these processes. Generally, the two processes for extraction and purification are carried out sequentially.

As described above, however, not any simple or efficient extraction process has been developed yet. Although the excellent nucleic acid purification process of the inventors has been proposed, the process should be done at two steps of extraction and purification so as to prepare nucleic acid. So as to rapidly carry out the treatment of a great number of samples, a nucleic acid preparation process for simultaneous purification together with simple and high efficient extraction has been desired.

SUMMARY OF THE INVENTION

It is an object of the invention to provide a process of extracting nucleic acid in a simple manner at a high efficiency from biological materials with no use of any hazardous reagent. Particularly, it is an object of the invention to provide a process of extracting nucleic acid in a simple manner with no use of any hazardous reagent from biological materials, particularly such as a bacteria of the genus *Mycobacterium*, having required specific procedures for nucleic acid extraction in biological samples such as feces having been said to involve much difficulty in the purification.

It is an additional object of the invention to provide a process of simultaneously carrying out the extraction and purification of nucleic acid from such biological materials in a simple manner.

The inventors made investigations. Consequently, the inventors have found that the objects can be achieved by vigorous agitation of biological materials with fine particles in solutions containing chelating reagents or agitation of biological materials with aqueous solutions containing chelating reagents and quaternary ammonium salts, together with organic solvents and fine particles. Thus, the invention has been achieved.

The invention includes the following inventions.

1. A process of extracting nucleic acid, comprising a step of agitating a biological material from which nucleic acid is to be extracted in the presence of fine particles in a solution containing a chelating reagent.

2. The process of extracting nucleic acid as described in the first aspect, where the chelating reagent is selected from the group consisting of polyaminocarboxylic acid and salts thereof.

3. The process of extracting nucleic as described in the first aspect, where the chelating reagent is selected from the group consisting of EDTA and reagents similar to EDTA.

4. The process of extracting nucleic acid as described in any one of the first to third aspects, where the chelating reagent is selected from the group consisting of ethylenediamine-N,N,N',N'-tetraacetic acid (EDTA), O,O'-bis(2-aminophenylethyleneglycol)ethylenediamine-N,N,N', N'-tetraacetic acid (BAPTA), N,N-bis(2-hydroxyethyl) glycine (Bicine), trans-1,2-diaminocyclohexane-ethylenediamine-N,N,N',N'-tetraacetic acid (CyDTA), 1,3-diamino-2-hydroxypropane-ethylenediamine-N,N,N',N'-tetraacetic acid (DPTA-OH), diethylenetriamine-N,N,N',N", N"-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl)ethylenediamine-N,N',N'-triacetic acid (EDTA-OH), ethylenediamine-N,N,N',N'-tetrakis (methylenephosphonic acid) (EDTPO), O,O'-bis(2-aminoethyl) ethyleneglycol tetraacetic acid (EGTA), N,N'-bis(2-hydroxybenzyl)ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N, N,N',N'-tetraacetic acid (methyl-EDTA), nitrilotriacetic acid (NTA), nitrilotripropionic acid (NTP), nitrilotris (methylenephosphonic acid) trisodium salt (NTPO), N,N, N',N'-tetrakis(2-pyridylmethyl)ethylenediamine (TPEN), and triethylenetetramine-N,N,N',N",N"-hexaacetic acid (TTHA).

5. The process of extracting nucleic acid as described in any one of the first to fourth aspects, where the concentration of the chelating reagent in the solution is 5 mM to 500 mM on the basis of the solution.

6. The process of extracting nucleic acid as described in any one of the first to fifth aspects, where the process never requires the use of phenol.

7. The process of extracting nucleic acid as described in any one of the first to sixth aspects, where the biological material is a virus, a bacterium, a fungus, a protozoa, a plant or an animal.

8. The process of extracting nucleic acid as described in the seventh aspect, where the bacterium belongs to the genus *Mycobacterium*.

9. The process of extracting nucleic acid as described in the eighth aspect, where the bacterium of the genus Mycobacterium is *Mycobacterium tuberculosis,* atypical *mycobacterium, Mycobacterium leprae, Mycobacterium paratuberculosis,* or Crohn Disease pathogenic microbe.

10. The process of extracting nucleic acid as described in any one of the first to ninth aspects, where the biological material is contained in a biological sample such as biological tissues, fluids, secreted substances and excreted substances or is contained in an environmental sample such as soil, water and air.

11. The process of extracting nucleic acid as described in the tenth aspect, where the biological sample is feces, sputum or blood of animals.

12. A process of simultaneously carrying out the extraction and purification of nucleic acid, comprising a step of agitating a biological material from which nucleic acid is to be extracted and purificated together with an aqueous solution containing a chelating reagent and a quaternary ammonium salt, an organic solvent and fine particles, to simultaneously carry out the extraction and purification of nucleic acid.

13. The process of simultaneously carrying out the extraction and purification of nucleic acid as described in the twelfth aspect, where the chelating reagent is selected from the group consisting of polyaminocarboxylic acid and salts thereof.

14. The process of simultaneously carrying out the extraction and purification of nucleic acid as described in the twelfth aspect, where the chelating reagent is selected from the group consisting of EDTA and reagents similar to EDTA.

15. The process of simultaneously carrying out the extraction and purification of nucleic acid as described in any one of the twelfth to fourteenth aspects, where the chelating reagent is selected from the group consisting of ethylenediamine-N,N,N',N'-tetraacetic acid (EDTA), O,O'-bis(2-aminophenylethyleneglycol)ethylenediamine-N,N,N', N'-tetraacetic acid (BAPTA), N,N-bis(2-hydroxyethyl) glycine (Bicine), trans-1,2-diaminocyclohexane-ethylenediamine-N,N,N',N'-tetra acetic acid (CyDTA), 1,3-diamino-2-hydroxypropane-ethylenediamine-N,N,N',N'-tetraacetic acid (DPTA-OH), diethylenetriamine-N,N,N',N", N"-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl)ethylenediamine-N,N',N'-triacetic acid (EDTA-OH), ethylenediamine-N,N,N',N'-tetrakis (methylenephosphonic acid) (EDTPO), O,O'-bis(2-aminoethyl) ethyleneglycol tetraacetic acid (EGTA), N,N'-bis(2-hydroxybenzyl)ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N, N,N',N'-tetraacetic acid (methyl-EDTA), nitrilotriacetic acid (NTA), nitrilotripropionic acid (NTP), nitrilotris (methylenephosphonic acid) trisodium salt (NTPO), N,N, N',N'-tetrakis(2-pyridylmethyl)ethylenediamine (TPEN), and triethylenetetramine-N,N,N',N",N"-hexaacetic acid (TTHA).

16. The process of simultaneously carrying out the extraction and purification of nucleic acid as described in any one of the twelfth to fifteenth aspects, where the concentration of the chelating reagent is 5 mM to 500 mM on the basis of the aqueous solution.

17. The process of simultaneously carrying out the extraction and purification of nucleic acid as described in any one of the twelfth to sixteenth aspects, where the quaternary ammonium salt is selected from the group consisting of hexadecyltrimethylammonium bromide, hexadecylpyridinium chloride, hexadimethrine bromide, hexafluorenium bromide and methylthiazolium bromide.

18. The process of simultaneously carrying out the extraction and purification of nucleic acid as described in any one of the twelfth to seventeenth aspects, where the concentration of the quaternary ammonium salt is 0.001 to 20% by weight on the basis of the aqueous solution.

19. The process of simultaneously carrying out the extraction and purification of nucleic acid as described in any one of the twelfth to eighteenth aspects, where the organic solvent is selected from the group consisting of chloroform, carbon tetrachloride, alcohols, aromatic hydrocarbons, ethers and ketones.

20. The process of simultaneously carrying out the extraction and purification of nucleic acid as described in any one of the twelfth to nineteenth aspects, where plural organic solvents mixed together at any ratio are used as the organic solvent.

21. The process of simultaneously carrying out the extraction and purification of nucleic acid as described in any one of the twelfth to twentieth aspects, where chloroform and alcohols mixed together at any ratio are used as the organic solvent.

22. The process of simultaneously carrying out the extraction and purification of nucleic acid as described in any one of the twelfth to twenty-first aspects, where the organic solvent is a mix solution of chloroform and butanol at a volume ratio of 7:3 to 9:1.

23. The process of simultaneously carrying out the extraction and purification of nucleic acid as described in any one of the twelfth to twenty-second aspects, where the amount of the organic solvent is 5 to 95% by volume on the basis of the aqueous solution.

24. The process of simultaneously carrying out the extraction and purification of nucleic acid as described in any one of the twelfth to twenty-third aspects, where the diameter of fine particles is 0.05 to 0.5 mm.

25. The process of simultaneously carrying out the extraction and purification of nucleic acid as described in any one of the twelfth to twenty-forth aspects, where fine particles of diameters 0.05 to 0.5 mm are used in mixture with particles of diameters above 0.5 mm at any ratio.

26. The process of simultaneously carrying out the extraction and purification of nucleic as described in any one of the twelfth to twenty-fifth aspects, where the process never requires the use of phenol.

27. The process of simultaneously carrying out the extraction and purification of nucleic acid as described in any one of the twelfth to twenty-sixth aspects, where the biological material is a virus, a bacterium, a fungus, a protozoa, a plant or an animal.

28. The process of simultaneously carrying out the extraction and purification of nucleic acid as described in the twenty-seventh aspect, where the bacterium belongs to the genus *Mycobacterium*.

29. The process of simultaneously carrying out the extraction and purification of nucleic acid as described in the twenty-eighth aspect, where the bacterium of the genus *Mycobacterium* is *Mycobacterium tuberculosis*, a typical mycobacterium, *Mycobacterium leprae*, *Mycobacterium paratuberculosis*, or Crohn Disease pathogenic microbe.

30. The process of simultaneously carrying out the extraction and purification of nucleic acid as described in any one of the twelfth to twenty-ninth aspects, where the biological material is contained in a biological sample such as biological tissues, fluids, secreted substances and excreted substances or is contained in an environmental sample such as soil, water and air.

31. The process of simultaneously carrying out the extraction and purification of nucleic acid as described in the thirtieth aspect, where the biological sample is feces, sputum or blood of animals.

32. The process of simultaneously carrying out the extraction and purification of nucleic acid as described in the thirty-first aspect, where the feces are derived from humans or cattle.

33. The process of simultaneously carrying out the extraction and purification of nucleic acid as described in the thirty-second aspect, where the cattle is cow, goat or sheep.

In this specification, the term nucleic acid means both DNA and RNA.

In accordance with the invention, nucleic acid can be extracted with no use of any hazardous reagents highly efficiently from biological materials from which nucleic acid is to be extracted. Particularly, nucleic acid can be extracted with no use of any hazardous reagents highly efficiently from biological materials such as bacteria of the genus *Mycobacterium* requiring specific procedures for extracting nucleic acid therein due to its difficulty in destructing the cell.

In accordance with the invention, additionally, a simple process of simultaneously carrying out the extraction and purification of nucleic acid from biological materials can be provided. Particularly, a simple process can be provided, for simultaneously carrying out the extraction and purification of nucleic acid with no use of any hazardous reagents from biological materials especially such as bacteria of the genus *Mycobacterium* having been required specific procedures for extracting nucleic acid therein due to its difficulty in destructing the cell, in the case that such biological materials exist in biological samples such as feces having been said to involve much difficulty in the purification.

DETAILED DESCRIPTION OF THE INVENTION

Figure 1:
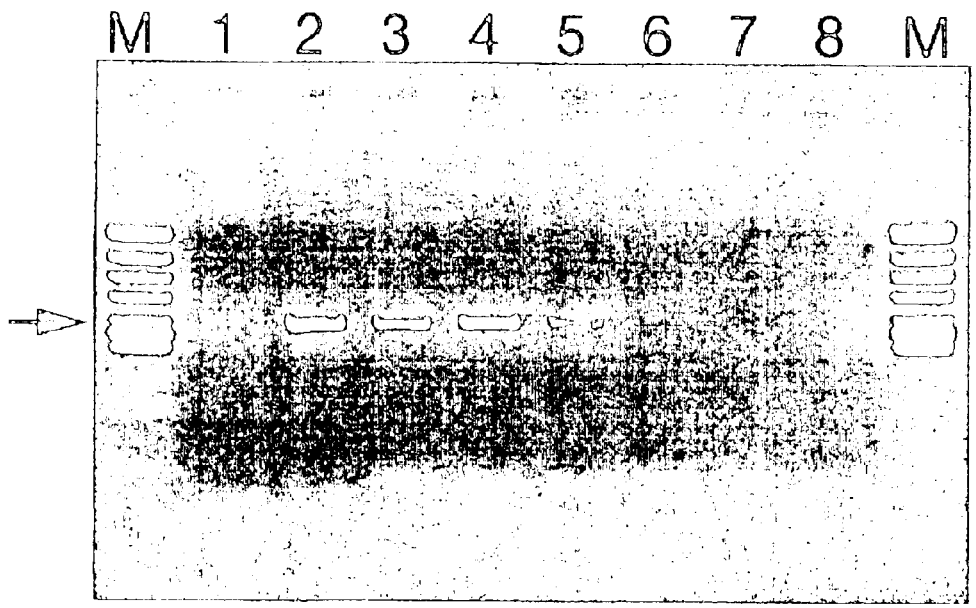
FIG. 1 shows the results of the detection of PCR reaction products by agarose gel electrophoresis, in case of using TE buffer and phenol as solution for extracting nucleic acid.
Figure 2:
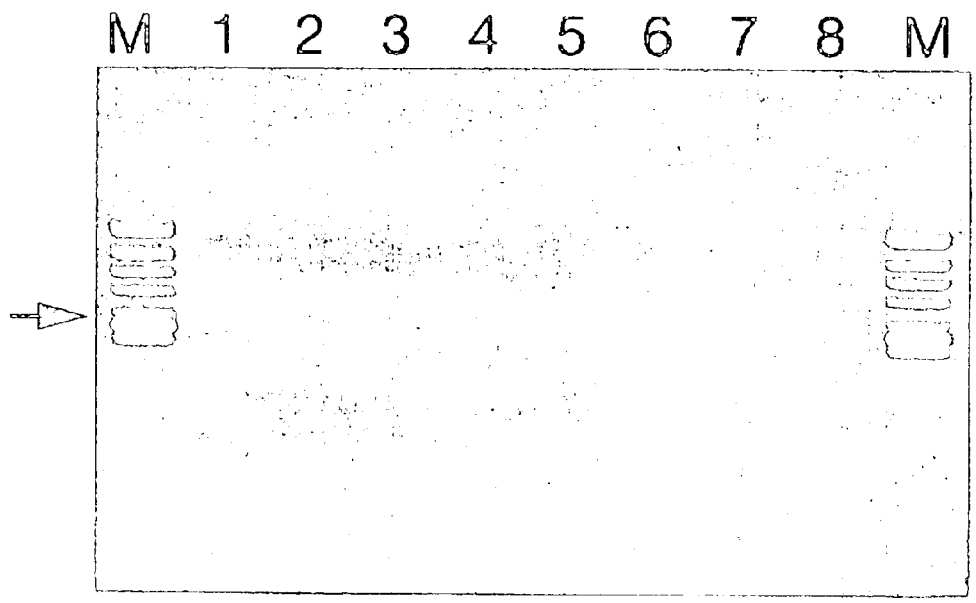
FIG. 2 shows the results of the detection of PCR reaction products by agarose gel electrophoresis, in case of using TE buffer as solution for extracting nucleic acid.
Figure 3:
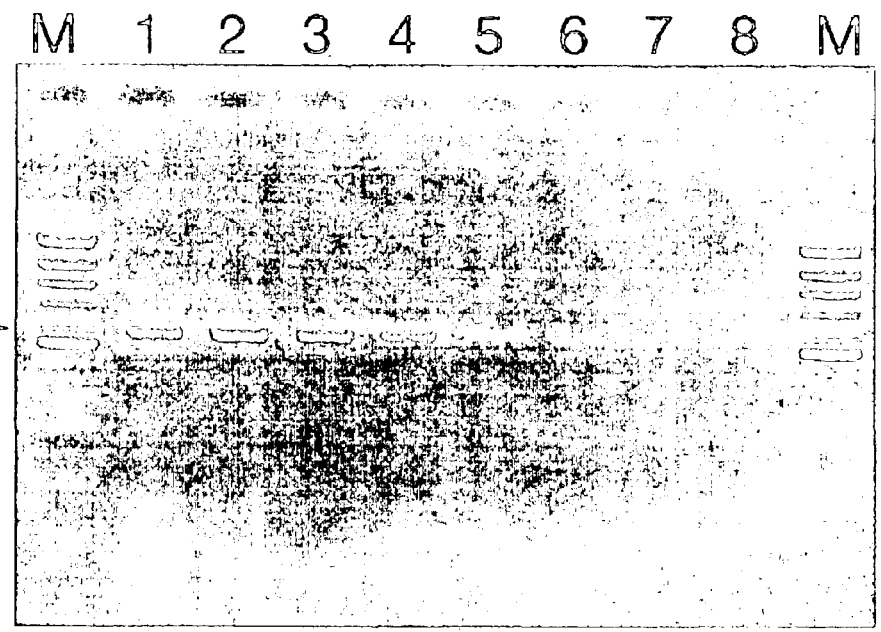
FIG. 3 shows the results of the detection of PCR reaction products by agarose gel electrophoresis, in case of using Tris buffer and phenol as solution for extracting nucleic acid.
Figure 4:
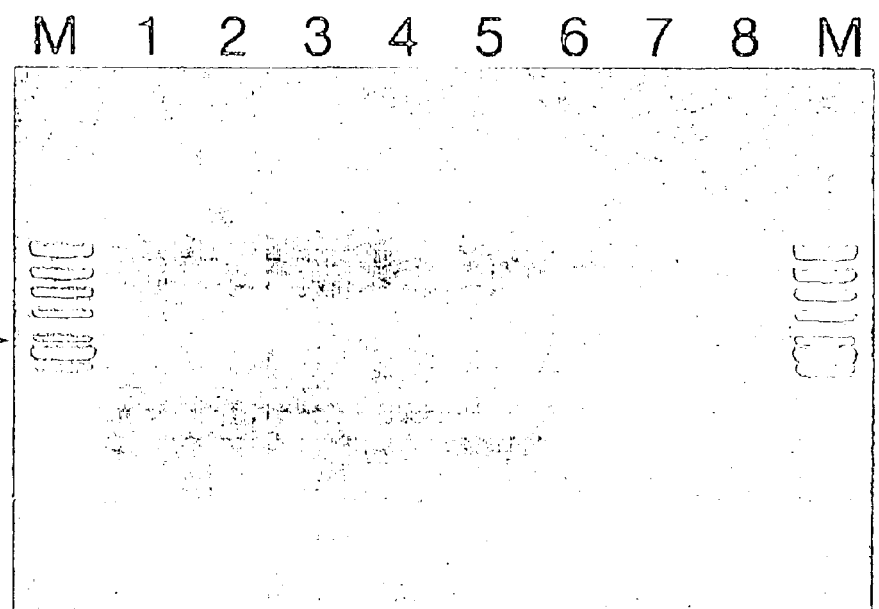
FIG. 4 shows the results of the detection of PCR reaction products by agarose gel electrophoresis, in case of using Tris buffer as solution for extracting nucleic acid.

The nucleic acid extraction process is first described.

According to the nucleic acid extraction process of the invention, a biological material is vigorously agitated in the presence of fine particles in a solution containing a chelating reagent, to extract nucleic acid in the solution.

The biological material for use in the nucleic acid extraction process of the invention includes but is not limited to viruses, bacteria, fungi, protozoa, plants and animals. The nucleic acid extraction process of the invention is useful particularly for biological materials involving much difficulty in cellular destruction, such as fungi and the bacteria of the genus *Mycobacterium*. The bacteria of the genus *Mycobacterium* include for example but are not limited to *Mycobacterium tuberculosis*, atypical *mycobacterium*; *Mycobacterium leprae*, *Mycobacterium paratuberculosis*, and Crohn Disease pathogenic microbe.

Samples containing such biological materials include for example but are not limited to biological tissues of animals and plants, biological samples such as feces, sputum and blood from cattle and humans, and environmental samples such as soil, water and air.

As the chelating agent for use in the nucleic acid extraction process of the invention, preferably, EDTA or polyaminocarboxylic acid similar to EDTA is used. Specifically, the chelating agent includes for example ethylenediamine-N,N,N',N'-tetraacetic acid (EDTA), O,O'-bis(2-aminophenylethyleneglycol)ethylenediamine-N,N,N',N'-tetraacetic acid (BAPTA), N,N-bis(2-hydroxyethyl)glycine (Bicine), trans-1,2-diaminocyclohexane-ethylenediamine-N,N,N',N'-tetraacetic acid (CyDTA), 1,3-diamino-2-hydroxy propane-ethylenediamine-N,N,N',N'-tetraacetic acid (DPTA-OH), diethylenetriamine-N,N,N',N'',N''-pentaacetic acid (DPTA), diethylenetriamine-N,N'-dipropionic acid dihydrochloride (EDDP), ethylenediamine-N,N'-bis(methylenephosphonic acid) hemihydrate (EDDPO), N-(2-hydroxyethyl)ethylenediamine-N,N',N'-triacetic acid (EDTA-OH), ethylenediamine-N,N,N',N'-tetrakis(methylenephosphonic acid) (EDTPO), O,O'-bis(2-aminoethyl)ethyleneglycol tetraacetic acid (EGTA), N,N'-bis(2-hydroxybenzyl)ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris(methylenephosphonic acid) trisodium salt (NTPO), N,N,N',N'-tetrakis(2-pyridylmethyl)ethylenediamine (TPEN), and triethylenetetramine-N,N,N',N'',N'''-hexaacetic acid (TTHA). These chelating reagents may be used singly or in combination of two or more thereof.

One factor for cell wall capable of retaining the structure includes the presence of calcium ion. These chelating reagents readily coordinate with calcium ion. These chelating reagents coordinate with the calcium ion on cell wall, to modify the structure of cell wall, so that cell wall cannot retain the structure any more, leading to ready destruction of cell wall.

On the basis of the solution, the chelating reagent in the solution is used at a concentration of for example 5 mM to 250 mM, preferably 10 mM to 250 mM according to the nucleic acid extraction process of the invention. When the concentration of the chelating reagent is below 5 mM, the destruction efficiency of cells is likely to be low. When the concentration is above 500 mM, additional treatment may sometimes be needed in the course of nucleic acid purification and desalting treatment after cell destruction.

The nucleic acid extraction process of the invention characteristically requires the use of chelating reagents but never requires the use of other denaturation agents such as phenol for cell destruction, as in the related art. This enables simple and safe nucleic acid extraction.

So as to improve the destruction efficiency of cells, fine particles are added for vigorous agitation according to the nucleic acid extraction process of the invention. The fine particles then used generally include for example glass bead and zirconium oxide with no biological involvement in cell suspensions. Generally, fine particles of a specific gravity of 2.0 or more, for example 2.3 to 6.3 and with a diameter of 0.01 mm to 0.9 mm are used, with no limitation. When the diameter is 1 mm or more, the destruction efficiency of cells is likely to be low.

The process of simultaneously carrying out the extraction and purification of nucleic acid is now described.

According to the process of simultaneously carrying out the extraction and purification of nucleic acid, such biological material is agitated for example in a tube together with an aqueous solution containing a chelating reagent and a quaternary ammonium salt, an organic solvent and fine particles.

The biological material for use in the process of simultaneously carrying out the extraction and purification of nucleic acid of the invention includes but is not limited to viruses, bacteria, fungi, protozoa, plants and animals. The nucleic acid extraction process of the invention is useful particularly for biological materials involving much difficulty in cellular destruction, such as fungi and the bacteria of the genus *Mycobacterium*. The bacteria of the genus *Mycobacterium* include for example but are not limited to *Mycobacterium tuberculosis*, a typical *mycobacterium*, *Mycobacterium leprae*, *Mycobacterium paratuberculosis*, and Crohn Disease pathogenic microbe.

These biological materials of the invention includes for example but is not limited to biological samples such as biological tissues, fluids, secreted substances and excreted substances, and environmental samples such as soil, water and air. The biological samples include for example but are not limited to animal feces, sputum and blood. According to the process of simultaneously carrying out the extraction and purification of nucleic acid, particularly, cattle and human feces are useful as the feces, with no limitation. Further, the cattle include but are not limited to cow, goat and sheet.

The aqueous solution for use in the process of simultaneously carrying out the extraction and purification in accordance with the invention includes for example but is not limited to pH buffer solutions such as phosphate buffer, Tris buffer and acetate buffer.

As the chelating agent for use in the process of simultaneously carrying out the extraction and purification in accordance with the invention, preferably, EDTA or polyaminocarboxylic acid similar to EDTA is used. Specifically, the chelating agent includes for example ethylenediamine-N,N,N',N'-tetraacetic acid (EDTA), O,O'-bis(2-aminophenylethyleneglycol)ethylenediamine-N,N,N',N'-tetraacetic acid (BAPTA), N,N-bis(2-hydroxyethyl)glycine (Bicine), trans-1,2-diaminocyclohexane-ethylenediamine-N,N,N',N'-tetraacetic acid (CyDTA), 1,3-diamino-2- hydroxy propane-ethylenediamine-N,N,N',N'-tetraacetic acid (DPTA-OH), diethylenetriamine-N,N,N',N",N"-pentaacetic acid (DPTA), diethylenetriamine-N,N'-dipropionic acid dihydrochloride (EDDP), ethylenediamine-N,N'-bis(methylenephosphonic acid) hemihydrate (EDDPO), N-(2-hydroxyethyl) ethylenediamine-N,N',N'-triacetic acid (EDTA-OH), ethylenediamine-N,N,N',N'-tetrakis(methylenephosphonic acid) (EDTPO), O,O'-bis(2-aminoethyl)ethyleneglycol tetraacetic acid (EGTA), N,N'-bis(2-hydroxybenzyl) ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris(methylenephosphonic acid) trisodium salt (NTPO), N,N,N',N'-tetrakis(2-pyridylmethyl)ethylenediamine (TPEN), and triethylenetetramine-N,N,N',N",N"-hexaacetic acid (TTHA). These chelating reagents may be used singly or in combination of two or more thereof.

One factor for cell wall capable of retaining the structure includes the presence of calcium ion. These chelating reagents readily coordinate with calcium ion. These chelating reagents coordinate with the calcium ion on cell wall, to modify the structure of cell wall, so that cell wall cannot retain the structure any more, leading to ready destruction of cell wall.

According to the process of simultaneously carrying out the extraction and purification of the invention, the chelating reagent is satisfactorily used at a concentration of for example 5 mM to 250 mM, preferably 10 mM to 250 mM on the basis of the aqueous solution. When the concentration of the chelating reagent is below 5 mM, the destruction efficiency of cells is likely to be low. When the concentration is above 500 mM, additional treatment may sometimes be needed for the process of the invention, where the purification of nucleic acid after cell destruction is simultaneously carried out.

The process of simultaneously carrying out the extraction and purification of the invention characteristically requires the use of chelating reagents but never requires the use of other denaturation agents such as phenol for cell destruction, as in the related art. This enables simple and safe nucleic acid extraction.

The quaternary ammonium salt for use in the process of simultaneously carrying out the extraction and purification of nucleic acid in accordance with the invention is onium salt containing cationic nitrogen atom N+, preferably with surfactant activity. Specifically, the quaternary ammonium salt includes for example but is not limited to hexadecyltrimethylammonium bromide, hexadecylpyridinium chloride, hexadimethrine bromide, hexafluorenium Bromide, and methylthiazolium bromide. For example, hydrophobic groups may appropriately be adjusted. These quaternary ammonium salts may be used singly or in combination of two or more thereof.

The quaternary ammonium salt is satisfactorily used at a concentration of 0.001 to 20% by weight, preferably 0.01 to 10% by weight on the basis of the aqueous solution. When the concentration is below 0.001% by weight, the effect of the quaternary ammonium salt on the purification is low. When the concentration is above 20% by weight, the quaternary ammonium salt is likely to be readily deposited.

The organic solvent for use in the process of simultaneously carrying out the extraction and purification of nucleic acid in accordance with the invention includes for example but is not limited to chloroform, carbon tetrachloride, alcohols, aromatic hydrocarbons such as benzene, ethers, and ketones. As such aromatic hydrocarbon, no use of highly hazardous phenol is rather preferable. Additionally, these organic solvents are preferably organic solvents immiscible with water at any ratio. Further, these organic solvents may be used singly or in combination of two or more thereof. A combination of chloroform and alcohol is preferable. A combination of chloroform and butanol is more preferable. Preferably, chloroform and butanol are combined together at a volume ratio of 7:3 to 9:1. In accordance with the invention, a mix solution of chloroform:butanol=8:2 (in volume ratio) is particularly useful.

Such organic solvent is preferably used at a volume of 5 to 95% by volume on the basis of the aqueous solution. However, the volume depends on the type of a subject biological material.

The use of such organic solvent enables efficient purification because contaminants in a biological material are readily incorporated in the organic solvent.

According to the process of simultaneously carrying out the extraction and purification of nucleic acid in accordance with the invention, a biological material is vigorously agitated in the presence of fine particles together with an organic solvent and a solution containing a chelating reagent and the quaternary ammonium salt. Fine particles added promote efficient destruction of cells because cells collide with the fine particles. As the fine particles then, fine particles of glass bead and zirconium oxide never biologically involved in cell suspension are generally used. Generally, fine particles of a specific gravity of 2.0 or more, for example 2.3 to 6.3 and with a diameter of 0.05 mm to 0.5 mm are used, with no limitation. When the diameter is 1 mm or more, the destruction efficiency of cells is likely to be low.

So as to improve the agitation efficiency to raise the cell destruction efficiency, particles of a diameter above 0.5 mm, for example particles of 1.0 mm to 2.0 mm may satisfactorily be used auxiliary, in addition to fine particles of a diameter within the above range. These particles of a diameter above 0.5 mm may be mixed with the fine particles of a diameter of 0.05 to 0.5 mm at any weight ratio. The resulting mixture is then used. As described above, the use of particles with different sizes can improve the agitation efficiency to induce cell collision with the particles at a high frequency.

According to the process of simultaneously carrying out the extraction and purification of nucleic acid in accordance with the invention, the sequence of adding the biological material, the chelating reagent, the quaternary ammonium salt, the organic solvent and the fine particles is not limited, as long as all these substances exist in a tube for agitation. For example, an aqueous solution is first prepared by dissolving a chelating agent and a quaternary ammonium salt in a pH buffer solution, which is then added to a tube containing a biological material, for suspension. To the resulting suspension are added an organic solvent and fine particles, for agitation. By these procedures, a person skilled in the art can appropriately adjust the timing for addition.

As described above, an intended nucleic acid can be recovered at high purity. By the process of simultaneously carrying out the extraction and addition of nucleic acid in accordance with the invention, the chelating agent and the fine particles destruct cell wall so that nucleic acid is extracted in water and is then purified with the quaternary ammonium salt and the organic solvent.

In the process of extracting nucleic acid and the process of simultaneously carrying out the extraction and purification of nucleic acid in accordance with the invention, the term nucleic acid means both DNA and RNA. Nucleic acids from bacteria, viruses and protozoa existing in animal feces, more specifically nucleic acids from bacteria, viruses and protozoa causing infectious diseases and existing in animal feces as well as nucleic acids from a typical cells such as tumor cells existing in animal feces can be recovered by these processes.

EXAMPLES

The invention will now be described in more detail in the following examples, which never have any meanings to limit the invention in any way.

[Procedure 1]

As a biological material, feces derived from a *paratuberculosis*-infected cow infected with *Mycobacterium paratuberculosis* causing *paratuberculosis* and belonging to the genus *Mycobacterium* were used.

First, 1 g of the feces derived from the paratuberculosis-infected cow was suspended in 10 mL of distilled water and was then left to stand for 5 minutes. The supernatant of 5 ml was recovered and centrifuged, to recover the feces pellet containing *Mycobacterium paratuberculosis*. A series of the procedures for recovering feces pellet was repeated four times, to recover four feces pellets.

Then, the following solutions for extracting nucleic acid were added to the resulting individual feces pellets, followed by additional addition of 800 mg of a glass bead of a diameter of 0.1 mm (specific gravity of 2.5). The resulting mixture was agitated (5,000 rpm for 3 minutes), using MINI-BEAD BEATER manufactured by BIOSPEC CO. After agitation with MINI-BEAD BEATER, the resulting mixture was centrifuged to recover the supernatant of 500 μl, which was then subjected to phenol/chloroform treatment and ethanol precipitation according to general purification and desalting concentration methods, to recover the pellet of nucleic acid.

(Solutions for Extracting Nucleic Acid)

Example A

750 μl of TE Buffer (10 mM Tris-HCl, 1 mM EDTA) and Phenol

Example B

750 μl of TE Buffer (10 mM Tris-HCl, 1 mM EDTA)

Comparative Example C

750 μl of Tris Buffer (10 mM Tris-HCl) and 750 μl of Phenol

Comparative Example D

750 μl of Tris Buffer (10 mM Tris-HCl)

The resulting individual pellets of nucleic acid were dissolved in 50 μl of distilled water. Using distilled water, then, 2-fold dilution series of the pellet solutions were prepared. To the individual 2-fold dilution series were added primers [of which the nucleotide sequences were GAT CGG AAC GTC GGC TGG TCA GG (Sequence No.1) and ACG ACG ACG CGC AGC GAT TGC TCT (Sequence No.2)] to amplify a partial region of IS900 as the gene specific to *Mycobacterium paratuberculosis,* Taq polymerase, dNTPs and a buffer solution for PCR under temperature conditions of 40 cycles of 97° C. for 30 seconds, 65° C. for 30 seconds, and 72° C. for 30 seconds.

After PCR, the reaction product was detected by procedures of agarose gel electrophoresis, ethidium staining, and photographic imaging with transilluminator, to examine the difference in the individual extraction efficiencies.

FIGS. 1, 2, 3 and 4 show the results of the detection of the reaction products in Examples A and B and Comparative Examples C and D. The PCR primers used in the experiments enable the recovery of a 362-bp reaction product when the IS900 gene exists. Lane 1 (left end) contains 25 μl of 50 μl of the solution of the nucleic acid pellet; lane 2 contains 12.5 μl thereof; lane 3 contains 6.3 μl thereof; lane 4 contains 3.1 μl thereof; lane 5 contains 1.6 μl thereof; lane 6 contains 0.8 μl thereof; lane 7 contains 0.4 μl thereof; and lane 8 contains 0.2 μl thereof. Additionally, lane M shows a molecular weight marker, which was prepared by digesting Φ×174 DNA with HincII. The extraction efficiency is higher in case that the reaction product is detected up to the utmost right lane where a smaller volume of the sample is contained.

Because phenol is used in Example A and Comparative Example C, the reaction product is detected up to lane 5 (FIG. 1) and lane 6 (FIG. 3), respectively, suggesting higher extraction efficiencies. Because the concentration of EDTA used was as low as 1 mM in Example B, no EDTA effect on nucleic acid extraction was observed, involving the detection of a very weak band alone on lane 1 (FIG. 2). Because no phenol or EDTA was used in Comparative Example D, only a very weak band was detected on lane 2. Thus, the extraction efficiency was poor (FIG. 4).

[Procedure 2]

By the same procedures as the procedure 1, first, 3 feces pellets containing Mycobacterium paratuberculosis were prepared. The solutions for extracting nucleic acid as shown below were added to the resulting individual feces pellets, followed by additional addition of 800 mg of a glass bead of a diameter of 0.1 mm (specific gravity of 2.5). The resulting mixture was agitated (5,000 rpm for 3 minutes), using MINI-BEAD BEATER manufactured by BIOSPEC CO. None of denaturing agents such as phenol was used in the procedure 2. After agitation with MINI-BEAD BEATER, the resulting mixture was centrifuged to recover the supernatant of 500 μl, which was then subjected to phenol/chloroform treatment and ethanol precipitation according to general purification and desalting concentration process, to recover the pellet of nucleic acid.

(Solutions for Extracting Nucleic Acid)

Example E

750 μl of Solution E (10 mM Tris-HCl, 5 mM EDTA)

Example F

750 μl of Solution F (10 mM Tris-HCl, 10 mM EDTA)

Example G

750 μl of Solution G (10 mM Tris-HCl, 100 mM EDTA)

The resulting individual pellets of nucleic acid were diluted sequentially, subjected to PCR reaction and were then treated by sequential procedures of agarose gel electrophoresis, ethidium staining, and photographic imaging with transilluminator by the same method as in the case of the procedure 1, to examine the difference in the individual extraction efficiencies of E to G.

Figure 5:
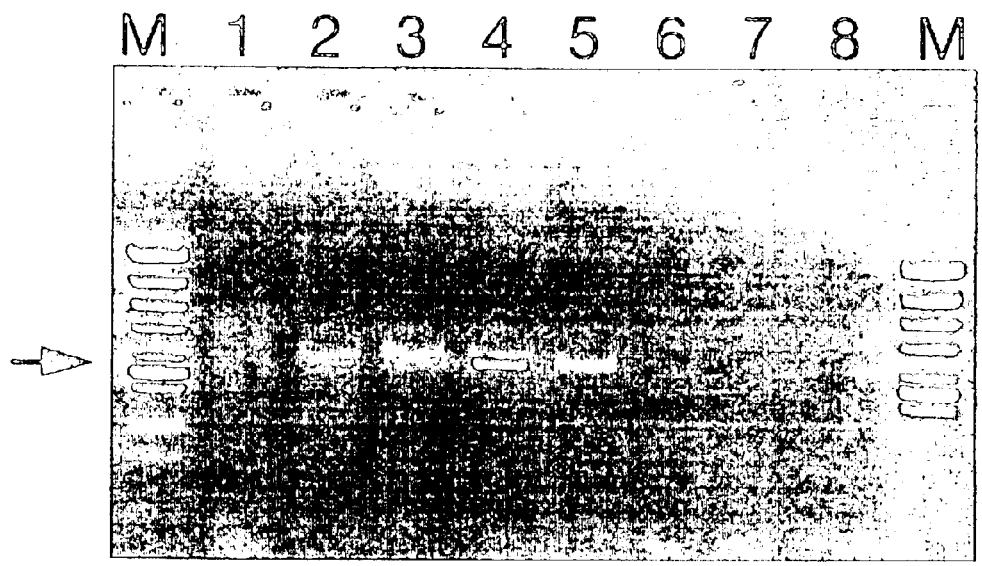
FIG. 5 shows the results of the detection of PCR reaction products by agarose gel electrophoresis, in case of using the solution E (10 mM Tris-HCl, 5 mM EDTA) as a solution for extracting nucleic acid.
Figure 6:
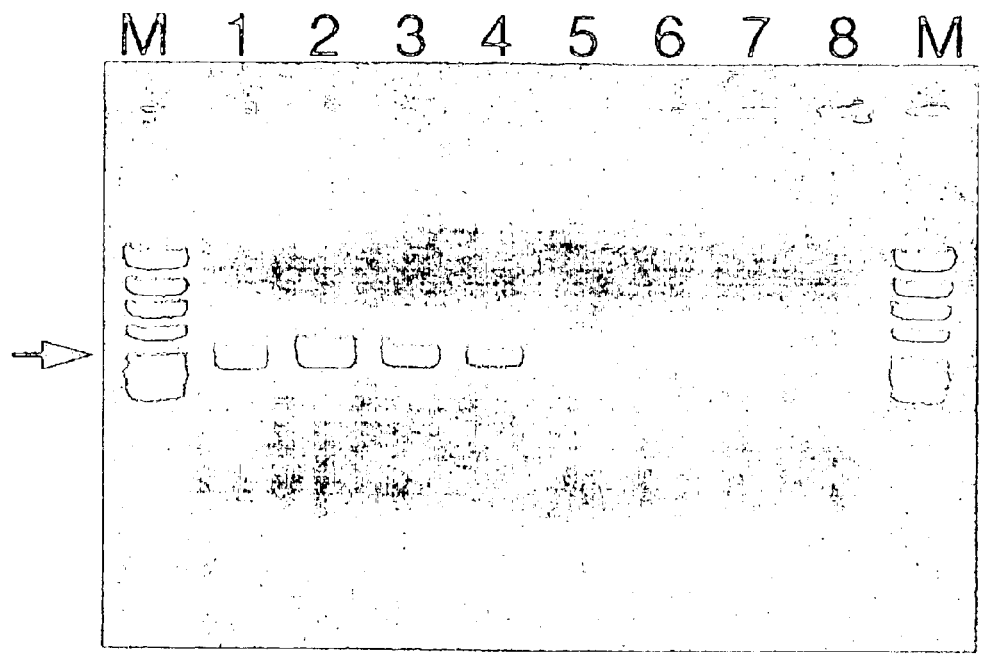
FIG. 6 shows the results of the detection of PCR reaction products by agarose gel electrophoresis, in case of using the solution F (10 mM Tris-HCl, 10 mM EDTA) as a solution for extracting nucleic acid.
Figure 7:
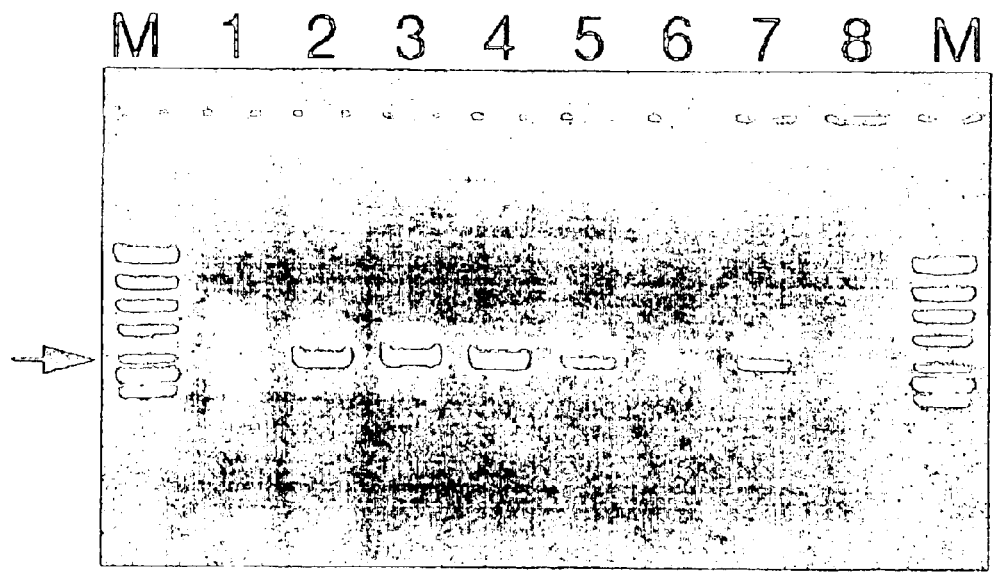
FIG. 7 shows the results of the detection of PCR reaction products by agarose gel electrophoresis, in case of using the solution G (10 mM Tris-HCl, 100 mM EDTA) as a solution for extracting nucleic acid.

FIGS. 5 to 7 show the results of the detection of the reaction products in Examples E to G. The reaction product was detected up to lane 5 in Example E using 5 mM EDTA in the solution for extraction (FIG. 5); up to lane 6 in Example F using 10 mM EDTA (FIG. 6); and up to lane 8 in Example G using 100 mM EDTA (FIG. 7). Consequently, a higher EDTA concentration led to higher extraction efficiency.

[Procedure 3]

By the same procedures as the procedure 1, first, 3 feces pellets containing Mycobacterium paratuberculosis were prepared. The solutions for extracting nucleic acid as shown below were added to the resulting individual feces pellets, followed by additional addition of 800 mg of a glass bead of a diameter of 0.1 mm (specific gravity of 2.5). The resulting mixture was agitated (5,000 rpm for 3 minutes), using MINI-BEAD BEATER manufactured by BIOSPEC CO. None of denaturing agents such as phenol was used in the procedure 3. After agitation with MINI-BEAD BEATER, the resulting mixture was centrifuged to recover the supernatant of 500 µl, which was then subjected to phenol/chloroform treatment and ethanol precipitation according to general purification and desalting concentration process, to recover the pellet of nucleic acid.

(Solutions for Extracting Nucleic Acid)

Example H

750 µl of Solution H (10 mM Tris-HCl, 100 mM CyDTA)

Example I

750 µl of Solution I (10 mM Tris-HCl, 100 mM EGTA)

The resulting individual pellets of nucleic acid were diluted sequentially, subjected to PCR reaction and were then treated by sequential procedures of agarose gel electrophoresis, ethidium staining, and photographic imaging with transilluminator by the same method as in the case of the procedure 1, to examine the difference in the individual extraction efficiencies of H and I.

Figure 8:
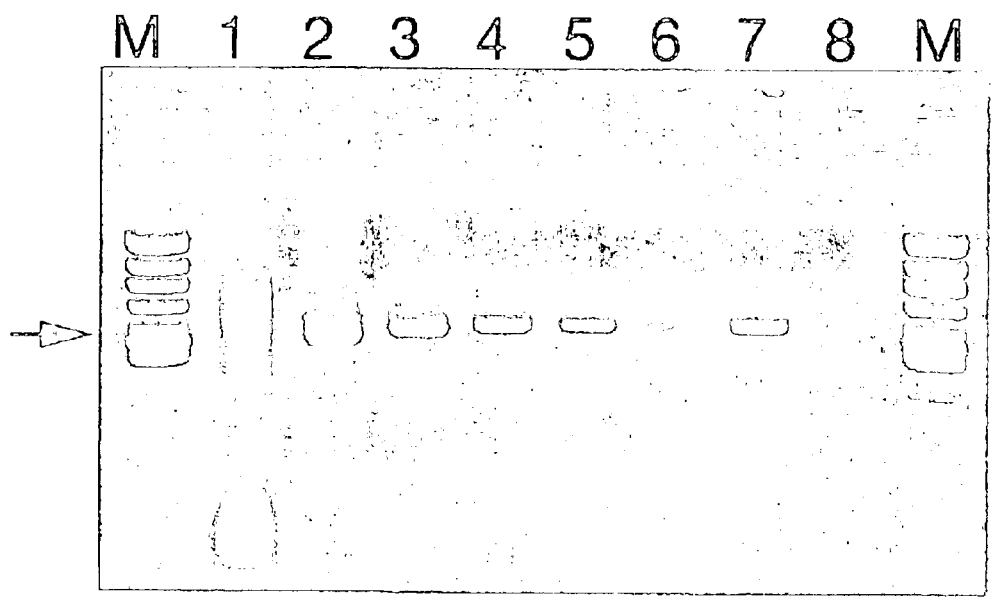
FIG. 8 shows the results of the detection of PCR reaction products by agarose gel electrophoresis, in case of using the solution H (10 mM Tris-HCl, 100 mM CyDTA) as a solution for extracting nucleic acid.
Figure 9:
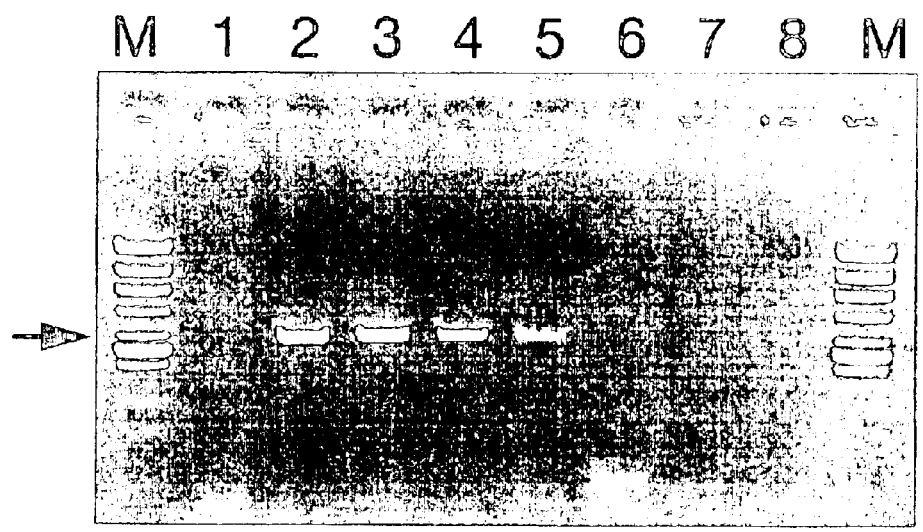
FIG. 9 shows the results of the detection of PCR reaction products by agarose gel electrophoresis, in case of using the solution I (10 mM Tris-HCl, 100 mM EGTA) as a solution for extracting nucleic acid.

FIGS. 8 and 9 show the results of the detection of the reaction products in Examples H and I. The reaction product was detected up to lane 7 in Example H using CyDTA in the solution for extraction (FIG. 8); and up to lane 5 in Example I using EGTA (FIG. 9). Consequently, the polyaminocarboxyl acid similar to EDTA also indicated high extraction efficiency like EDTA.

Example J

First, 1 g of the feces derived from the paratuberculosis-infected cow was suspended in 10 mL of distilled water and was then left to stand for 5 minutes. The supernatant of 5 ml was recovered and centrifuged, to recover the feces pellet containing Mycobacterium paratuberculosis.

Then, an aqueous solution of the following composition was prepared: 10 mM Tris-HCl, 100 mM EDTA, 1% by weight of hexadecyltrimethylammonium bromide, and 700 mM NaCl. 1 ml of the aqueous solution and 2 ml of a mix solution of chloroform and butanol [chloroform:butanol=8:2 (in volume ratio)] were added to a tube containing the feces pellets. Further, 3.0 g each of glass beads of a diameter of 0.1 mm and a diameter of 2.0 mm (specific gravity of 2.5) as fine particles was added to the tube. The resulting mixture was agitated with a vortex mixer (2,500 rpm for 60 minutes). The agitated sample was centrifuged at 10,000 G for 5 minutes, from which 500 µl of the supernatant was recovered to recover nucleic acid pellets by ethanol precipitation.

The resulting individual pellets of nucleic acid were diluted sequentially, subjected to PCR reaction and were then treated by sequential procedures of agarose gel electrophoresis, ethidium staining, and photographic imaging with transilluminator by the same method as in the case of the procedure 1.

Figure 10:
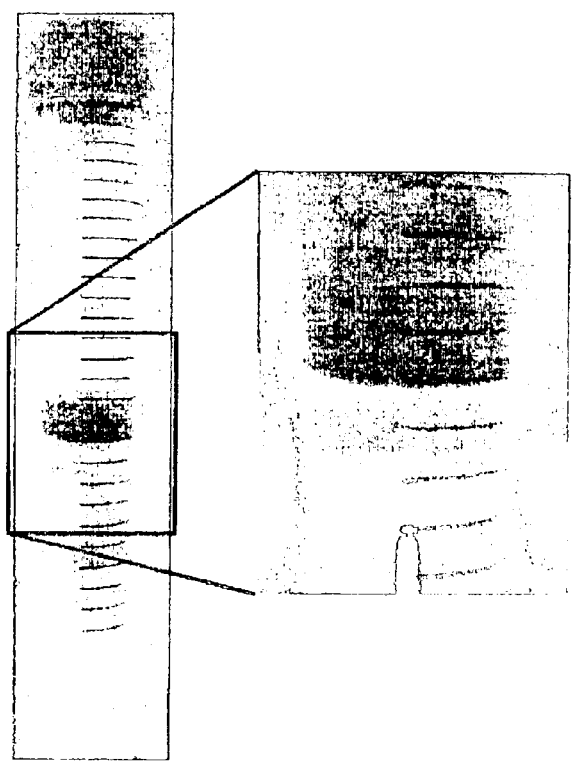
FIG. 10 shows a photopicture of a sample in a tube before agitation with a vortex mixer.
Figure 11:
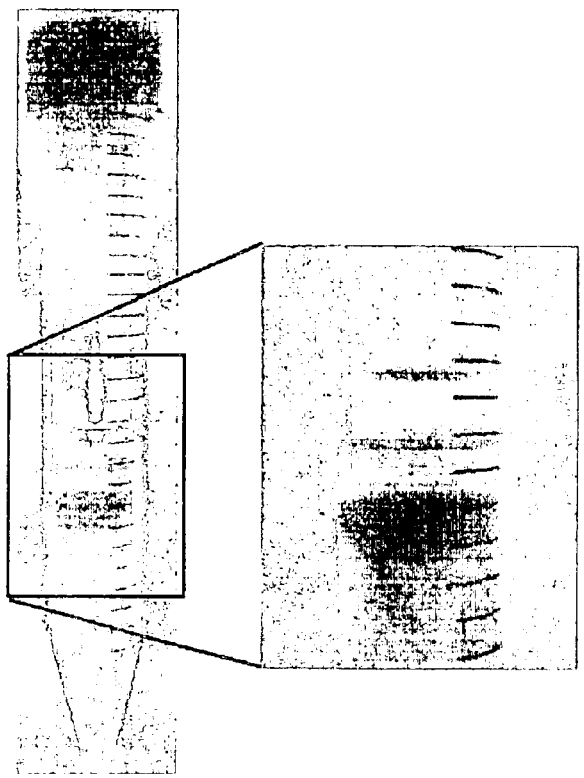
FIG. 11 shows a photopicture of a sample in a tube after agitation with a vortex mixer and centrifugation procedure.

FIG. 10 shows the photopicture of the sample in the tube before agitation with the vortex mixer, while FIG. 11 shows the photopicture of the sample in the tube after agitation with the vortex mixer and the centrifugation procedure. In FIG. 10, the aqueous layer (upper layer) was colored due to the feces ingredient. In FIG. 11, the dye component in the feces transferred to the organic layer (lower layer), indicating the completion of the purification.

Figure 12:
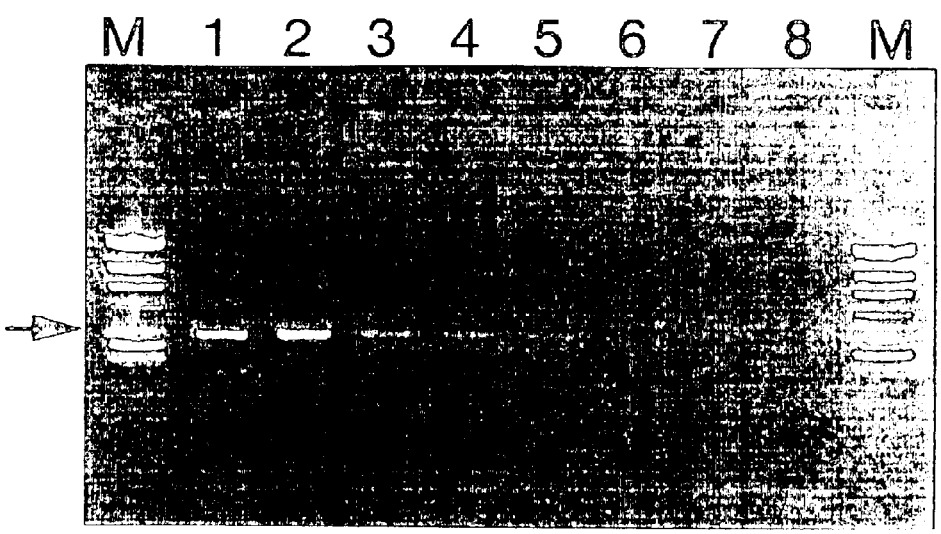
FIG. 12 shows the results of the detection of the PCR reaction product in Example J by agarose gel electrophoresis.

FIG. 12 shows the results of the detection of the PCR reaction product. On lane 1 to lane 5 and lane 8 was detected the 362-bp product. This indicates that the nucleic acid in Mycobacterium paratuberculosis in feces was extracted and simultaneously purified at an extent to enable PCR reaction.

What is claimed is:

1. A process of extracting nucleic acid, comprising a step of agitating a biological material from which nucleic acid is to be extracted in the presence of fine particles in a solution containing a chelating reagent wherein said process never requires the use of phenol.

2. The process of extracting nucleic acid according to claim 1, where the chelating reagent is selected from the group consisting of polyaminocarboxylic acid and salts thereof.

3. The process of extracting nucleic acid according to claim 1, where the chelating reagent is selected from the group consisting of EDTA and reagents similar to EDTA.

4. The process of extracting nucleic acid according to claim 1, where the chelating reagent is selected from the group consisting of ethylenediamine-N,N,N',N'-tetraacetic acid (EDTA), O,O'-bis(2-aminophenylethyleneglycol) ethylenediamine-N,N,N',N'-tetraacetic acid (BAPTA), N,N-bis(2-hydroxyethyl) glycine (Bicine), trans-1,2-diaminocyclohexane-ethylenediamine-N,N,N',N'-tetraacetic acid (CyDTA), 1,3-diamino-2-hydroxypropane-ethylenediamine-N,N,N',N'-tetraacetic acid (DPTA-OH), diethylenetriamine-N,N,N',N'',N''-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl) ethylenediamine-N,N',N'-triacetic acid (EDTA-OH), ethylenediamine-N,N,N',N'-tetrakis(methylenephosphonic acid) (EDTPO), O,O'-bis(2-aminoethyl)ethyleneglycol tetraacetic acid (EGTA), N,N'-bis(2-hydroxybenzyl) ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris (methylenephosphonic acid) trisodium salt (NTPO), N,N,N',N'-tetrakis(2-pyridylmethyl)ethylenediamine (TPEN), and triethylenetetramine-N,N,N',N'',N''-hexaacetic acid (TTHA).

5. The process of extracting nucleic acid according to claim 1, where the concentration of the chelating reagent in the solution is 5 mM to 500 mM on the basis of the solution.

6. The process of extracting nucleic acid according to claim 1, where the biological material is a virus, a bacterium, a fungus, a protozoa, a plant or an animal.

7. The process of extracting nucleic acid according to claim 6, where the bacterium belongs to the genus *Mycobacterium*.

8. The process of extracting nucleic acid according to claim 7, where the bacterium of the genus *Mycobacterium* is *Mycobacterium tuberculosis,* atypical mycobacterium, *Mycobacterium leprae, Mycobacterium paratuberculosis,* or Crohn Disease pathogenic microbe.

9. The process of extracting nucleic acid according to claim 1, where the biological material is contained in a biological sample such as biological tissues, fluids, secreted substances and excreted substances or is contained in an environmental sample such as soil, water and air.

10. The process of extracting nucleic acid according to claim 9, where the biological sample is feces, sputum or blood of animals.

11. A process of simultaneously carrying out the extraction and purification of nucleic acid, comprising a step of agitating together an aqueous solution containing a chelating reagent and a quaternary ammonium salt, an organic solvent and fine particles, to simultaneously carry out the extraction and purification of nucleic acid, wherein said process never requires the use of phenol.

12. The process of simultaneously carrying out the extraction and purification of nucleic acid according to claim 11, where the chelating reagent is selected from the group consisting of polyaminocarboxylic acid and salts thereof.

13. The process of simultaneously carrying out the extraction and purification of nucleic acid according to claim 11, where the chelating reagent is selected from the group consisting of EDTA and reagents similar to EDTA.

14. The process of simultaneously carrying out the extraction and purification of nucleic acid according to claim 11, where the chelating reagent is selected from the group consisting of ethylenediamine-N,N,N',N'-tetraacetic acid (EDTA), O,O'-bis(2-aminophenylethyleneglycol) ethylenediamine-N,N,N',N'-tetraacetic acid (BAPTA), N,N-bis(2-hydroxyethyl) glycine (Bicine), trans-1,2-diaminocyclohexane-ethylenediamine-N,N,N',N'-tetraacetic acid (CyDTA), 1,3-diamino-2-hydroxypropane-ethylenediamine-N,N,N',N'-tetraacetic acid (DPTA-OH), diethylenetriamine-N,N,N',N'',N''-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl) ethylenediamine-N,N',N'-triacetic acid (EDTA-OH), ethylenediamine-N,N,N',N'-tetrakis (methylenephosphonic acid) (EDTPO), O,O'-bis(2-aminoethyl) ethyleneglycol tetraacetic acid (EGTA), N,N'-bis(2-hydroxybenzyl) ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris(methylenephosphonic acid) trisodium salt (NTPO), N,N,N',N'-tetrakis(2-pyridylmethyl)ethylenediamine (TPEN), and triethylenetetramine-N,N,N',N'',N''-hexaacetic acid (TTHA).

15. The process of simultaneously carrying out the extraction and purification of nucleic acid according to claim 11, where the concentration of the chelating reagent is 5 mM to 500 mM on the basis of the aqueous solution.

16. The process of simultaneously carrying out the extraction and purification of nucleic acid according to claim 11, where the quaternary ammonium salt is selected from the group consisting of hexadecyltrimethylammonium bromide, hexadecylpyridinium chloride, hexadimethrine bromide, hexafluorenium bromide and methylthiazolium bromide.

17. The process of simultaneously carrying out the extraction and purification of nucleic acid according to claim 11, where the concentration of the quaternary ammonium salt is 0.001 to 20% by weight on the basis of the aqueous solution.

18. The process of simultaneously carrying out the extraction and purification of nucleic acid according to claim 11, where the organic solvent is selected from the group consisting of chloroform, carbon tetrachloride, alcohols, aromatic hydrocarbons, ethers and ketones.

19. The process of simultaneously carrying out the extraction and purification of nucleic acid according to claim 11, where plural organic solvents mixed together at any ratio are used as the organic solvent.

20. The process of simultaneously carrying out the extraction and purification of nucleic acid according to claim 11, where chloroform and alcohols mixed together at any ratio are used as the organic solvent.

21. The process of simultaneously carrying out the extraction and purification of nucleic acid according to claim 11, where the organic solvent is a mix solution of chloroform and butanol at a volume ratio of 7:3 to 9:1.

22. The process of simultaneously carrying out the extraction and purification of nucleic acid according to claim 11, where the amount of the organic solvent is 5 to 95% by volume on the basis of the aqueous solution.

23. The process of simultaneously carrying out the extraction and purification of nucleic acid according to claim 11, where the diameter of fine particles is 0.05 to 0.5 mm.

24. The process of simultaneously carrying out the extraction and purification of nucleic acid according to claim 11, where fine particles of diameters 0.05 to 0.5 mm are used in mixture with particles of diameters above 0.5 mm at any ratio.

25. The process of simultaneously carrying out the extraction and purification of nucleic acid according to claim 11, where the biological material is a virus, a bacterium, a fungus, a protozoa, a plant or an animal.

26. The process of simultaneously carrying out the extraction and purification of nucleic acid according to claim 25, where the bacterium belongs to the genus *Mycobacterium*.

27. The process of simultaneously carrying out the extraction and purification of nucleic acid according to claim 26, where the bacterium of the genus *Mycobacterium* is *Mycobacterium tuberculosis,* atypical *mycobacterium, Mycobacterium leprae, Mycobacterium paratuberculosis,* or Crohn Disease pathogenic microbe.

28. The process of simultaneously carrying out the extraction and purification of nucleic acid according to claim 11, where the biological material is contained in a biological sample such as biological tissues, fluids, secreted substances and excreted substances or is contained in an environmental sample such as soil, water and air.

29. The process of simultaneously carrying out the extraction and purification of nucleic acid according to claim 28, where the biological sample is feces, sputum or blood of animals.

30. The process of simultaneously carrying out the extraction and purification of nucleic acid according to claim 29, where the feces are derived from humans or cattle.

31. The process of simultaneously carrying out the extraction and purification of nucleic acid according to claim 30, where the cattle is cow, goat or sheep.

* * * * *

UNITED STATES PATENT AND TRADEMARK OFFICE
CERTIFICATE OF CORRECTION

PATENT NO.       : 6,852,495 B2
APPLICATION NO.  : 10/448394
DATED            : February 8, 2005
INVENTOR(S)      : Kouichi Kojima It is certified that error appears in the above-identified patent and that said Letters Patent is hereby corrected as shown below:

In the Assignee:

The Second Assignee's name was incomplete:

AGRICULTURE, FORESTRY AND FISHERIES TECHNICAL INFORMATION

SOCIETY

Signed and Sealed this

Twenty-third Day of January, 2007

JON W. DUDAS
*Director of the United States Patent and Trademark Office*